United States Patent [19]

Wild

[11] 4,017,614
[45] Apr. 12, 1977

[54] COMPOSITIONS FOR THE RELIEF OF MIGRAINE

[76] Inventor: Henry Wild, 8 Winster Place, Mereside, Blackpool, Lancashire, England

[22] Filed: Dec. 5, 1975

[21] Appl. No.: 638,006

Related U.S. Application Data

[63] Continuation of Ser. No. 504,781, Sept. 10, 1974, abandoned, which is a continuation of Ser. No. 301,906, Oct. 31, 1972, abandoned, which is a continuation of Ser. No. 95,361, Dec. 4, 1970, abandoned.

[30] Foreign Application Priority Data

Dec. 5, 1969  United Kingdom ............ 59643/69

[52] U.S. Cl. .............. 424/232; 424/250; 424/260; 424/324
[51] Int. Cl.$^2$ ....................... A61K 31/625
[58] Field of Search ........................... 424/232, 250

[56] References Cited
FOREIGN PATENTS OR APPLICATIONS 705,979  2/1952  United Kingdom

OTHER PUBLICATIONS

Kunkle, Current Therapy (1959) pp. 514–517.
Wolff et al., Current Therapy (1952) pp. 621–622.
Goodman et al., Phar. Basis of Thera. (1965) pp. 326, 332, & 333.
Merck Index, 8th Edition (1968) pp. 5, 8, 12, 13, 172, 276, 336, 929, and 930.
Physicians Desk Reference (PDR) (1968) p. 1136.
Parsonage, "Current Therapy" (1970) pp. 634–636.
Handbook of Non-Prescription Drugs (1973) Edition, APHA, pp. 32–35.

Primary Examiner—Norman A. Drezin
Attorney, Agent, or Firm—Sughrue, Rothwell, Mion, Zinn & Macpeak

[57] ABSTRACT

The invention is predicated on the discovery that certain 1,4-disubstituted piperazines interact synergistically with certain known analgesics to antagonize or block the stimulus causing migraine. This effect is most pronounced when administering a mixture of 1-p-chlorobenzhydryl-4-p-(tertiary butyl)-benzyl-piperazine (buclizine) and N-acetyl-p-aminophenol (paracetamol) in the respective proportions by weight of from 1:20 to 1:200.

16 Claims, No Drawings

COMPOSITIONS FOR THE RELIEF OF MIGRAINE

This application is a continuation application of Ser. No. 504,781, filed Sept. 10, 1974, in turn a continuation application of Ser. No. 301,906, filed Oct. 31, 1972, in turn a continuation application of Ser. No. 95,361, filed Dec. 4, 1970, all of said prior applications being abandoned.

BACKGROUND OF THE INVENTION

This invention relates to pharmacologically useful compositions.

In British Pat. No. 705,979 there are described a number of unsymmetrical 1,4-diaralkyl piperazines. In particular such piperazines may have as the aralkyl substituent upon one nitrogen atom a p-halobenzhydryl group and as the aralkyl substituent upon the second nitrogen atom a benzyl or an alkyl- or dialkyl-benzyl group the alkyl group or groups being present as the substituent or substituents in the benzene ring. Such compounds have been recognised to possess properties characteristic of an antihistamine. Nevertheless such compounds have been found to possess properties unusual in an antihistamine, for example, their prolonged period of activity which, in relation to typical antihistamine properties has been shown to persist for a number of days. Thus in relation to guinea pigs it has been shown that 1-p-chlorobenzhydryl-4-p-tertiary butyl-benzyl piperazine gives protection against histamine in the form of an aerosol for as long as 16 days.

Antihistamines are administered primarily to give protection against various conditions which are recognized to have an allergic origin and, upon the basis that certain patients suffering from migraine do so as the result of an allergic reaction to food which they have consumed, a limited investigation has been reported in which migraine induced by the consumption of food was sought to be prevented by the prophylactic administration of 1-p-chlorobenzhydryl-4-p-tertiary-butyl-benzyl piperazine: prevention was however claimed in but a single case and as a pain-reducing agent the treatment was regarded as unsuccessful. Elsewhere it has been stated that antihistamines are valueless in the treatment of migraine.

It is an object of the invention to provide a pharmaceutical composition of substantially non-toxic character which can be taken by patients who suffer from migraine with at least a reasonable prospect of obtaining relief or, if taken in time, to prevent the occurrence of a migraine attack.

SUMMARY OF THE INVENTION

According to the present invention there is provided a pharmaceutical composition for the control of migraine which comprises (a) a 1,4-disubstituted piperazine having the general formula:

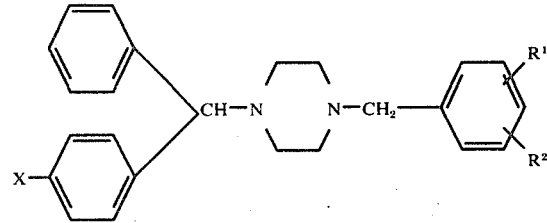

wherein X is a hydrogen atom, chlorine or bromine and $R'$ and $R^2$ each represent a hydrogen atom or an alkyl group having not more than six carbon atoms, at least one of $R'$ and $R^2$ being an alkyl group, or a salt of said piperazine and (b) N-acetyl-p-aminophenol, p-ethoxyacetanilide, salicylamide or acetylsalicylic acid, the 1,4-disubstituted piperazine and the compound (b) being respectively present in the weight ratio of 1:20 to 1:200. Preferably the weight ratio is 1:40 to 1:120 and most preferably 1:70 to 1:100.

The 1,4-disubstituted piperazines used in accordance with the present invention have as a substituent in the 4-position a nuclear substituted benzyl group in which the nuclear substituent or substituents is or are one or two alkyl groups present in the 3-, 4- or 5-positions. The alkyl group or groups each contain one to six carbon atoms. When two alkyl groups are present these may be the same or different groups. When the alkyl group or groups has or have three to six carbon atoms they may be straight or branched chain alkyl groups. Thus the substituent on the 4-nitrogen atom may be para-methylbenzyl, meta-methylbenzyl, para(n-butyl)-benzyl, para-(tertiary-butyl)benzyl, meta-(tertiary-butyl)benzyl or a 3,5-dimethylbenzyl group.

Preferably the substituted piperazine is a 1-p-chlorobenzhydryl-4-alkylbenzyl-piperazine. Specific examples of 1,4-disubstituted piperazines which may be used include 1-p-chlorobenzhydryl-4-p-methylbenzyl-piperazine, 1-p-chlorobenzhydryl-4-m-methylbenzylpiperazine, 1-p-chlorobenzhydryl-3,5-dimethylbenzylpiperazine, 1-p-chlorobenzhydryl-4-p-(tertiarybutyl)benzylpiperazine, 1-p-bromobenzhydryl-4-p-(tertiarybutyl)benzylpiperazine and 1-p-chlorobenzhydryl-4-m-(tertiarybutyl)benzylpiperazine. These compounds are all di-acid bases and are most conveniently handled in the form of salts thereof with pharmaceutically acceptable acids such as hydrochloric acid, phosphoric acid, lactic acid, maleic acid, fumaric acid or tartaric acid. The above compounds may be prepared by the methods described in British Pat. specification No. 705,979.

The second essential component of the composition is N-acetyl-p-amino-phenol, salicylamide, acetylsalicylic acid or p-ethoxyacetanilide. All these compounds will be recognized as well-known analgesics which can be regarded as phenol derivatives. The present invention is based upon the discovery that these particular analgesics act synergistically in some way with the antihistamines referred to above to antagonize or block the stimulation causing migraine. This synergistic effect is not found with other analgesics which have been tested and is most pronounced in the case of N-acetyl-p-amino-phenol (paracetamol) and the most preferred combination is paracetamol and 1-p-chlorobenzhydryl-4-p-(tertiary butyl)benzyl-piperazine (buclizine). A mixture of the analgesics may be used as component (b) of the composition.

The weight ratio in which the two essential ingredients are present is an important feature of the invention. It has been found that the 1,4-disubstituted piperazine is only required in quite a small proportion by weight relative to the selected analgesic. This proportion is 1:20 to 1:200 by weight, more preferably 1:40 to 1:120, and even more preferably 1:70 to 1:100.

In view of the nature of migraine it is highly desirable that the composition of the present invention be available in a form in which it is readily self-administered and accordingly tablets, capsules and suppositories are the preferred forms for the medicament.

For an individual weighing about 10 stone the aim should be to administer sufficient of the composition to provide about 2.5 to 24 milligrams, preferably 8 to 15 milligrams, e.g., 12.5 milligrams, of one of the 1,4-disubstituted piperazines prior to or at least at the first signs of onset of an attack of migraine. This quantity is most desirably spread over two or even three tablets or capsules which should be taken one at a time.

The nature of the effect produced by the combined administration of the components of the compositions is not fully understood but is quite different from that observed when the 1,4-disubstituted piperazines are administered alone.

It is believed that the analgesic serves to potentiate the 1,4-disubstituted piperazine. However, since the duration of effect of the analgesic is shorter than that of the fully potentiated 1,4-disubstituted piperazine, when the relief given by the analgesic wears off the symptoms of the migraine may, in certain instances, reoccur and may even escape further control. Thus in order to maintain the analgesic level it may be necessary if the pain reoccurs to administer additional analgesic alone at intervals after the first dose of the combined administration of the components of the composition. The amount of analgesic employed in the subsequent doses may be the same as that employed in the initial dose. For example, if the total amounts of 1,4-disubstituted piperazine and analgesic administered in the initial dose are 12.5 mg. and 1000 mg. respectively, a suitable dose of analgesic in each of the subsequent administrations may be 1000 mg.

The subsequent doses may be taken at 3 to 4 hourly intervals after the first dose but only if necessary to maintain relief of pain.

In trials which have been carried out with compositions prepared in accordance with the invention, a success rate of approximately 90% has been reported by patients who took the tabletted compositions while anticipating or actually experiencing a migraine attack. Experience so far has shown that the compositions are most effective if taken before a migraine attack becomes established. Many migraine sufferers have an aura or premonition that they are about to experience a migraine attack and the composition should be taken as soon as this occurs. In other patients, migraine attacks may be associated with particular events such as car journeys and in these cases the compositions should be taken prophylactically prior to such events. An advantageous feature of the compositions of the invention is that their prophylactic effect appears to last for a considerable period, in some patients apparently up to 3 days.

The preferred dose of analgesic depends upon the particular compound selected. In the case of paracetamol, salicylamide and acetylsalicylic acid, the preferred dose is 300 to 1000 mg. while for p-ethoxyacetanilide (phenacetin) the preferred dose is 300 to 600 mg.

The compositions of this invention may contain other analgesics in addition to the analgesic selected as component (b). A derivative of the 3-methyl ether of morphine (codeine) in an amount ranging from 7.5 to 22.5 mg./1 gm. of the component (b) or dextropropoxyphene in an amount ranging from 12.5 to 37.5 mg./1 gm. of the component (b) are especially preferred.

The most preferred 1,4-disubstituted piperazine is 1-p-chlorobenzhydryl-4-p-(tertiary butyl)benzyl piperazine which is also known as buclizine. It is especially preferred in the form of the dihydrochloride.

Increasing the amount of 1,4-disubstituted piperazine beyond the recommended amount, surprisingly, does not bring about an increase in the relief obtained. In fact, it has been found that if the 1,4-disubstituted piperazine is administered in amounts significantly in excess of 25 mg. the symptoms of the migraine may become more pronounced and a full migraine may develop which cannot be controlled by the administration of further analgesic.

It has been found that control of migraine is not achieved if the active ingredients of the compositions are administered separately at different times even if the interval between administering the separate ingredients is as short as 30 minutes. However the desired effect is obtained if the active ingredients are formulated separately in the specified relative proportions and the separate formulations administered substantially simultaneously. It is therefore within the scope of the present invention to provide a packaged pharmaceutical which comprises a 1-p-chlorobenzhydryl-4-p-alkylbenzyl-piperazine formulated in dosage unit form and packaged together with an analgesic selected from N-acetyl-p-aminophenol, p-ethoxyacetanilide, salicylamide, or acetylsalicylic acid formulated separately in dosage unit form, the dosage unit of the 1,4-disubstituted piperazine being between 2.5 and 24 mg. and the dosage unit of said analgesic being between 20 and 200 times the dosage unit of said 1,4-disubstituted piperazine. The 1,4-disubstituted piperazine and analgesic may be formulated, for example, as tablets or capsules and packaged together in pairs in a "bubble pack," the tablets or capsules possibly being identified by coloring to aid the patient in reliably selecting a tablet or capsule containing one of the active ingredients and another containing the other active ingredient.

In a further embodiment, the two essential active ingredients may be formulated in a single dosage form but with each active ingredient confined to a separate portion of the dosage form. For example the dosage form may comprise a gelatin capsule having an internal wall dividing the capsule into separate compartments one of which is filled with a formulation containing one ingredient and the other containing the other active ingredient. In use the internal wall would be ruptured or dissolved by fluid in the stomach and both active ingredients released simultaneously.

Normally it will be more convenient to formulate the compositions of the invention into a single dosage unit form which may include tablets, capsules, suspensions, syrups, and suppositories. Such dosage forms may be prepared in the following manner.

1. TABLETS

Buclizine dihydrochloride is triturated with the powdered binding agent. It is then mixed with paracetamol (N-acetyl-p-aminophenol) and passed through a 60 mesh sieve. Water, containing any necessary colors dissolved within it, is mixed in with these powders. Sufficient gelatinized starch paste is also added to bind the powders together. The resulting mix is granulated through a 10 mesh screen. The granules formed are dried in an oven at 50° C. and then passed through a 16 mesh screen.

Codeine phosphate is triturated with the necessary glidants, lubricants and disintegrating agents, and if required, any pigments, and the whole is then mixed with the granules. These granules are then compressed on a conventional tabletting machine.

2. SUSPENSION

Codeine phosphate and buclizine dihydrochloride are dissolved in a distilled water. The paracetamol in finely powdered form is mixed with a further portion of water which contains sufficient of a suitable suspending agent dissolved within it. Any colors, preservatives, buffering agents and flavors are added to a further portion of the water. All portions of water are then mixed together and made to volume.

3. SYRUP

Paracetamol is dissolved in the required amount of propylene glycol and glycerin. Codeine phosphate and buclizine dihydrochloride are dissolved in the necessary quantity of water. The two portions are mixed together, the ratios of the portions being such that the solids remain dissolved in their respective solvent. Preservatives, flavors, buffering agents and colors are then added in aqueous solution, the whole then being made to volume.

4. HARD CAPSULES

Buclizine dihydrochloride and codeine phosphate are triturated together with paracetamol. A suitable lubricant, for example, magnesium stearate is added and mixed. The whole is then passed through a fine mesh screen and remixed. The resulting powder is then filled into hard gelatin capsules on a conventional capsulating machine.

5. SOFT GELATIN CAPSULES

The active ingredients in powder form, together with preservatives, buffering agents, are added to the necessary amount of fixed oil containing sufficient of a mixture of a hydrogenated oil and beeswax to suspend the powders. The whole is passed through a suitable mill and remixed. This mixture is then de-aerated and then encapsulated on a conventional encapsulating machine.

6. SUPPOSITORIES

The active ingredient in fine powdered form are added to the correct amount of suppository base which has previously been warmed to a temperature just above its melting point. The powders are dispersed in the melted base by use of a suitable stirrer. It may be necessary to then pass this molten mass through a mill. This will depend on particle size. The suppository mass is then moulded into suitable shaped suppositories.

The following Examples are given to illustrate the invention:

EXAMPLE I

Tablets were formulated containing buclizine (as its dihydrochloride) and paracetamol in the quantities specified in the following table.

| Formulation Number | Buclizine per tablet (mg.) | Paracetamol per tablet (mg.) |
| --- | --- | --- |
| 1 | 6.25 | 500 |
| 2 | 5 | 500 |
| 3 | 3.75 | 500 |
| 4 | 10 | 500 |

In preparing the tablets the buclizine dihydrochloride was triturated with powdered starch to form a free-flowing powder. The resulting powder was mixed with the paracetamol in the appropriate porportions and the mixture passed through a 60 mesh sieve. Water was mixed in and then sufficient gelatinized starch paste added to bind the granules together. The resulting mix was granulated through a 10 mesh screen, dried at 50° C. and then passed through a 16 mesh screen. The resulting granules after assaying for concentration of the active ingredients, were compressed on a conventional tabletting machine. The normal dosage of the resulting tablets is 1 to 3 tablets.

EXAMPLE II

Tablets were prepared containing:

| | |
| --- | --- |
| Buclizine hydrochloride | 6.25 mg. |
| Paracetamol | 500 mg. |
| Codeine phosphate | 7.5 mg. |

The tablets were prepared in the manner described in Example I except that the codeine phosphate was triturated with the dried granules containing buclizine and paracetamol and the resulting mixture tabletted.

The following specific experience has been obtained in treating migraine sufferers with the tablets prepared in Example II. In each case the dosage given was two tablets per administration.

CASE 1 (FEMALE) AGE 43

Has suffered attacks for the last 5 years, the migraine being associated always with the menstrual period. Symptoms — intense headache and nausea. The patient is always incapacitated for 1 or 2 days. Prescribed medicines gave unsatisfactory results.

The patient took a "dose" at the first signs of the migraine which prevented it from developing. No incapacitation resulted.

CASE 2 (MALE) AGE 58

Suffered migraine for 20 years. These attacks occur at least once in 2 weeks and they always occur at weekends. The patient usually waking Saturday mornings suffering from a violent headache; the other symptoms of classical migraine soon follow. The patient has to remain in bed, in a darkened room, for the remainder of the day. The patient found that since taking one "dose" on Friday nights, when retiring, no attacks of migraine have occurred.

CASE 3 (MALE) AGE 53

Patient suffered migraine since the age of 15. Attacks occur now at 4 to 6 week intervals. The prominent predromal symptom is incomplete vision followed, after 15 to 20 minutes by intense intercranial pain, inability to focus, think or speak coherently. These last ½ to ¾ hours leaving the patient with a dull ache at the base of the neck and an almost overwhelming feeling of lethargy.

The patient now takes the "dose" as soon as the predromal symptoms occur; this stops the migraine from developing. A mild feeling of tiredness is apparent for ½ to ¾ hour.

CASE 4 (FEMALE) AGE 60

Migraine first occured at 12 years of age; attacks occur once every 1 or 2 weeks. Symptoms are classical migraine associated with intense nausea and vomitting. Symptoms last up to 12 hours. Patient now takes the "dose" as soon as possible when the attack starts. This prevents the attack developing although a certain amount of mild head pain can remain.

CASE 5 (FEMALE) AGE 61

Attacks first occurred in the early 20's. They always, as now, are precipitated by a particular event, e.g., a journey or social occasion. The migraine starts as general headache, intensifying to right hemicranial severe pain. Nausea is prominent but vomitting does not occur.

Patient now takes a "dose" prior to travelling or social gathering and is not troubled by migraine, although on several occasions, a mild headache has occurred.

I claim:

1. A method for preventing or diminishing the severity of a migraine attack of a migraneous individual comprising prophylactically administering to said individual after onset of an aura or premonition of a migraine attack by said individual or during an episodic pattern of migraine attacks, a composition comprising:
   a. 1-p-chlorobenzhydryl 4-p-(tertiary butyl)-benzyl piperazine or a pharmaceutically acceptable addition salt of said piperazine and (b) a compound selected from the group consisting of N-acetyl-p-aminophenol, p-ethoxy-acetanilide, salicylamide and acetylsalicylic acid, the piperazine (a) and the compound (b) being respectively present in a weight ratio of 1:20 to 1:200, the dosage unit of said piperazine (a) ranging from 2.5 to 24 mg.

2. A method for preventing or diminishing the severity of a migraine attack of a migraneous individual comprising prophylactically administering to said individual after onset of an aura or premonition of a migraine attack by said individual or during an episodic pattern of migraine attacks, a composition comprising component (a) 1-p-chlorobenzhydryl 4-p-(tertiary butyl)-benzyl piperazine or a pharmaceutically acceptable addition salt of said piperazine and as component (b) at least two compounds selected from the group consisting of N-acetyl-p-aminophenol, p-ethoxy-acetanilide, salicylamide and acetylsalicylic acid, the dosage unit of said piperazine (a) ranging from 2.5 to 24 mg., the piperazine (a) and said component (b) being respectively present in a weight ratio 1:20 to 1:200.

3. A method for preventing or diminishing the severity of a migraine attack by a migraneous individual comprising prophylactically administering to said individual after onset of an aura or premonition of a migraine attack by said individual or during an episodic pattern of migraine attacks, a composition comprising (a) 1-p-chlorobenzhydryl 4-p-(tertiary butyl)-benzyl piperazine in an amount of 2.5 to 24 mg., (b) 200 to 1500 mg. of N-acetyl-p-aminophenol and (c) 7.5 to 22.5 mg. of codeine per 1 gram of said N-acetyl-p-aminophenol.

4. A method for preventing or diminishing the severity of a migraine attack of a migraneous individual comprising prophylactically administering to said individual after onset of an aura or a premonition of a migraine attack by said individual or during an episodic pattern of migraine attacks, a composition comprising (a) 2.5 to 24 mg. of 1-p-chlorobenzhydryl 4-p-(tertiary butyl)-benzyl piperazine and (b) 200 to 1500 mg. of N-acetyl-p-aminophenol.

5. The method of claim 2, wherein said piperazine (a) and said component (b) are present in relative proportions by weight within the range 1:40 to 1:120, respectively.

6. The method of claim 5, wherein said range is from 1:70 to 1:100.

7. The method of claim 2, in which the component (b) is present in an amount of from 200 to 1500 mg.

8. The method of claim 7, wherein the component (b) is present in an amount of from 300 to 1000 mg.

9. The method of claim 3 wherein said piperazine (a) and said N-acetyl-p-aminophenol (b) are present in relative proportions by weight within the range of 1:40 to 1:120, respectively.

10. The method of claim 9, in which said range is from 1:70 to 1:100.

11. The method of claim 3, wherein said N-acetyl-p-aminophenol is present in an amount of from 200 to 1500 mg.

12. A method for preventing or diminishing the severity of a migraine attack of a migraneous individual comprising prophylactically administering to said individual after onset of an aura or premonition of a migraine attack by said individual or during an episodic pattern of migraine attacks, a composition comprising component (a) 1-p-chlorobenzhydryl 4-p-(tertiary butyl)-benzyl piperazine or a pharmaceutically acceptable addition salt of said piperazine, component (b) at least wo compounds selected from the group consisting of N-acetyl-p-aminophenol, p-ethoxyacetanilide, salicylamide and acetylsalicylic acid and as component (c) codeine, the dosage unit of said piperazine (a) ranging from 2.5 to 24 mg., the piperazine (a) and said component (b) being respectively present in a weight ratio of 1:20 to 1:200, the amount of codeine being from 7.5 to 22.5 mg. per 1 gram of said component (b).

13. The method of claim 12 wherein said piperazine (a) and said component (b) are present in relative proportion by weight within the range 1:40 to 1:120, respectively.

14. The method of claim 13, wherein said range is from 1:70 to 1:100.

15. The method of claim 12 in which component (b) is present in an amount of from 200 to 1500 mg.

16. The method of claim 15 wherein said component (b) is present in an amount of from 300 to 1000 mg.

* * * * *